United States Patent [19]
Roy et al.

[11] Patent Number: 5,739,314
[45] Date of Patent: Apr. 14, 1998

[54] METHOD FOR SYNTHESIZING 2'-O-SUBSTITUTED PYRIMIDINE NUCLEOSIDES

[75] Inventors: Saroj Roy, Acton; Jin-Yan Tang, Shrewsbury, both of Mass.

[73] Assignee: Hybridon, Inc., Cambridge, Mass.

[21] Appl. No.: 846,124

[22] Filed: Apr. 25, 1997

[51] Int. Cl.$^6$ .............................. C07H 1/00; C07H 1/02; C07H 11/067
[52] U.S. Cl. ........................................ 536/55.3; 536/25.3
[58] Field of Search ................................... 536/55.3, 25.3

[56] References Cited

U.S. PATENT DOCUMENTS 5,214,135   5/1993   Srivastava et al. ................... 536/26.7

OTHER PUBLICATIONS

*Antisense Research and Application* (Crooke and Lebleu, eds., CRC Press, Boca Raton, FL, 1993).
Cummins et al., "Characterization of fully 2'-modified oligoribonucleotide hetero-and homoduplex hybridization and nuclease sensitivity," *Nucleic Acids Research* 23, 2019 (1995).
Gin and Dekker, "The Preparation and Properties of O-Methylated Adenosine Derivatives," *Biochemistry* 7, 1413 (1968).
Haines, Synthesis of 1-(2'-O-Methyl-β-D-Ribofuranosyl)-Uracil (2'-O-Methyluridine) and 3-(2'-O-Methyl-β-D-Ribofuranosyl)Uracil *Tetrahedron* 29, 2807-2810 (1973).
Hodge et al., "Simplified Synthesis of 2'-O-Alkyl Ribopyrimidines," *Tetrahedron Letters* 36(17), 2933-2936 (1995).
Kawai et al., Conformational Rigidity of Specific Pyrimidine Residues in tRNA Arises from Posttranscriptional Modifications that Enhance Steric Interaction between the Base and the 2'-Hydroxyl Group, *Biochemistry* 31, 1040 (1992).
Kikugawa and Ichino, "Studies on the Vilsmeier-Haack Reaction," *J. Org. Chem.* 37, 284-288 (1972).
Lesnick et al., "Oligodeoxynucleotides Containing 2'-O-Modified adenosine: Synthesis and Effects on Stability of DNA:RNA Duplexes," *Biochemistry* 32, 7832 (1993).
McGee and Zhai, "Reaction of Anhydronucleosides with Magnesium Alkoxides: Regiospecific Synthesis of 2'-O-Alkylpyrimidine Nucleosides," *Nucleosides & Nucleotides* 15, 1797-1803 (1996).

Nyilas et al., "Synthesis of $O^{2'}$-Methylcytidine, $N^4$, $O^{2'}$-Dimethylcytidine and $N^4$, $N^4$,$O^{2'}$-Trimethylcytidine from a Common Intermediate," *Acta Chemica Scandinavica* B 40, 826-830 (1986).
Pathak and Cattopadadhyaya, "Preparation of 2'-O-methyl Ethers of Adenosine and Uridine Using 2',3'-O-(dibutylstannylene) Nucleosides and Diazomethane," *Chemica Scripta* 26, 135-139 (1986).
Robbins et al., "Nucleic Acid Related Compounds," *J. Org. Chem.* 39, 1891-1899 (1974).
Spraot, "Synthesis of 2'-O-Alkyloligoribonucleotides," in *Methods in Molecular Biology: Protocols for Oligonucleotides and Analogs* (vol. 20) (S. Agrawal, Ed., Humana Press, Totowa, NJ, 1993).
Sproat and Lamond, in "2'-O-Methyloligoribonucleotides: synthesis and applications," *Oligonucleotides and Analogues: A Practical Approach* (F. Eckstein, Ed., Oxfoed University Press 1991).
Uhlmann and Peymann, "Antisense oligonucleotides: A New Therapeutic Principle," *Chem. Rev.* 90, 543 (1990).
Verheyden et al., "Synthesis of Some Pyrimidine 2'-Amino-2'-deoxynucleosides," *J. Org. Chem.* 36, 250-254 (1971).
Wagner et al., "Preparation and Synthetic Utility of Some Organotin Derivatives of Nucleosides," *J. Org. Chem.* 39, 24 (1974).
Wagner et al., "A simple procedure for the preparation of protected 2'-O-methyl or 2'-O-ethyl ribonucleoside-3'-O-phosphoramidites," *Nucleic Acids Res.* 19, 5965 (1991).
Yamauchi, "Methylation Study of Ribonucleosides, Deoxyribonucleosides, and 2'-O-Methylribonucleosides with Trimethylsulphonium Hydroxide and Trimethylsulphonium Iodide. Influence of the 2'-Hydroxy-groups on the Reactivity of the Base Moieties of Ribonucleosides," *Perkin I* 2787-2792 (1980).

*Primary Examiner*—Gary L. Kunz
*Attorney, Agent, or Firm*—McDonnell Boehnen Hulbert & Berghoff

[57] ABSTRACT

The present invention provides an improved method of synthesizing 2'-O—R substituted pyrimidine mononucleosides. The method comprises reacting an anhydropyrimidine with magnesium alkoxide in the corresponding alcohol at elevated temperatures to directly produce the 2'-O—R substituted pyrimidine nucleoside product. The method advantageously eliminates several steps from prior art methods, thereby reducing the time and cost of synthesis and increasing the yield of final product.

6 Claims, No Drawings

METHOD FOR SYNTHESIZING 2'-O-SUBSTITUTED PYRIMIDINE NUCLEOSIDES

BACKGROUND OF THE INVENTION

1. Field of the Invention

This invention relates to improved methods of synthesizing protected 2'-O-substituted pyrimidine nucleosides.

2. Description of the Related Art

Novel oligonucleotide analogues containing modified bases have proven to be valuable antisense probes. The presence of 2'-O-alkyl ribonucleosides in oligonucleotides has been shown to decrease both chemical and enzymatic degradation of oligonucleotides while retaining or even increasing the recognition of complementary target sequences. (Cummins et al., *Nucleic Acids Research* 23:2019, 1995; Lesnick et al., *Biochemistry* 32:7832, 1993; Kawai, et al., *Biochemistry* 31:1040, 1992). These properties of 2'-O-alkyl oligonucleotides make them extremely useful in ribozymes and antisense oligonucleotides. See, e.g., *Antisense Research and Applications* (Crooke and Lebleu, Eds., CRC Press, Boca Raton, Fla., 1993).

2'-O-methyl ribonucleosides have been prepared by partial methylation of a nucleoside with diazomethane and also by partial tritylation of uridine, methylation of the products and removal of N-alkylated isomers. (Haines, *Tetrahedron* 29:2807–2810, 1973).

2'-O-methyl nucleosides have also been prepared by using trimethylsulphonium hydroxide ($Me_3SOH$) and trimethylsulphonium iodide ($Me_3SI$) at elevated temperature, yielding 2'- and 3'-O-alkylated nucleoside. (Yamauchi, *Perkin I* 2787–2792, 1980).

A variety of $N^3$-protected ribonucleosides have been subject to alkylation of the ribose hydroxyls (wherein the order of reactivity is 2'-OH>3'-OH>5'-OH). E.g., Gin and Dekker, *Biochemistry* 7:1413 1968. Similar problems are inherent in base-promoted alkylation of cytidine. (Wagner, et al., *Nucleic Acids Res.* 19: 5965, 1991). Methyl iodide and silver oxide reaction on $N^3$-protected 3',5'-O-bis silylated nucleoside gave the product but included four extra steps, thereby decreasing the overall yield. (Suresh and Saroj, U.S. Pat. No. 5,214,135).

Tin-catalyzed reactions of unprotected uridine with either alkyl halides (Wagner et al., *J. Org. Chem.* 39:24, 1974) or diazomethane (Robbins et al., *J. Org. Chem.* 39: 1891, 1974) directly produced both 2' and 3'-O-alkyl nucleosides in high yield.

These and a variety of other methods are not selective for 2'-O-alkylation and require chromatographic or other methods of separation to isolate the desired 2'-O-alkyl nucleosides, thereby increasing the time and expense of the synthesis while greatly decreasing its efficiency and overall yield. See, e.g., Wagner, et al., *J. Org. Chem.* 39:24, 1974; Robbins et al., *J. Org. Chem.* 39:1891–1899, 1974; and Pathak and Chattopadadhyaya, *Chemica Scripta* 26:135–139, 1986.

Sproat and Lamond, in *Oligonucleotides and Analogues: A Practical Approach* (F. Eckstein, Ed., Oxford University Press 1991) describes a multi-step synthesis of 2'-O-methylribonucleosides employing a silyl blocking group at the 3' and 5' positions. Sproat, in *Methods in Molecular Biology: Protocols for Oligonucleotides and Analogs* (Vol. 20) (S. Agrawal, Ed., Humana Press, Totowa, N.J., 1993) describe a similar multi-step synthesis of 2'-allyl ribonucleotides.

Recently, McGee and Zhai, *Nucleosides & Nucleotides* 15:1797–1803, 1996, reported selective alkylation of 5'-O-dimethoxytrityl (DMT) anhydrouridine with either magnesium or calcium alkoxide in DMF at 100° C. Although initial yields of the desired product were high, subsequent steps to convert the protected 2'-O-alkyluridine to the cytidine analog resulted in a significant drop in yield. Furthermore, attempts to react the unprotected anhydrouridine with magnesium methoxide under the same conditions to produce 2'-O-methyluridine failed.

Because of the ever increasing interest in using 2'-O-substituted nucleosides in antisense oligonucleotides and elsewhere, there remains a desire for faster and more efficient methods of synthesizing 2'-O-methylated nucleosides.

SUMMARY OF THE INVENTION

The present invention discloses improved methods that provide for faster and more productive synthesis of 2'-O—R substituted pyrimidine nucleosides (wherein R is allyl or $C_1$–$C_3$ alkyl (i.e., methyl, ethyl, or propyl)), the method comprising reacting anhydrouridine or anhydrocytidine with $Mg(OR)_2$ in corresponding alcohols (R—OH) to produce 2'-O—R substituted uridine or 2'-O—R substituted cytidine, respectively.

The present method provides an unexpected improvement over prior art methods such as disclosed by McGee and Zhai, supra. The advantages of the present method arise from several factors, including the elimination of the necessity to block the 3'- and/or 5'-hydroxyl of the pyrimidine mononucleoside (e.g., with bis-silylating reagent or DMT) before the alkylation reaction as well as the ability to conduct the reaction in corresponding alcohols. Without the need to block the $N^3$, 3'-, and/or 5'-hydroxyls two steps are eliminated. McGee and Zhai observed no reaction of the unprotected pyrimidine nucleoside.

The ability to conduct the reaction in alcohol also eases synthesis because divalent alkoxides are synthesized in alcohols. The need to isolate $Mg(OR)_2$ is thereby eliminated. Thus, the present method comprises a one-pot synthesis. The method of McGee and Zhai, for example, entails synthesis of magnesium alkoxide in corresponding alcohols and its subsequent isolation and transfer to a DMF-containing reaction vessel for synthesis of the 2'-O-substituted pyrimidine nucleoside.

A further advantage of the present method is the shorter time to completion of alkylation reactions. Although methods such as those reported by McGee and Zhai took 4 hours at 1 gram scale, an increase in scale to 10 grams required 3 times longer. In the present invention, the reaction was completed in 5 hours at a scale of from 5 grams to 75 grams.

The efficiency of production of 2'-O-alkylcytidine is increased dramatically by the present method because it is direct from anhydrocytidine rather than from 2'-O-alkyluridine, which McGee and Zhai reported resulted in only 50% yield.

The foregoing merely summarizes certain aspects of the present invention and is not intended, nor should it be construed, as limiting the invention in any manner. All patents and other publications are hereby incorporated by reference in their entirety.

DETAILED DESCRIPTION OF THE INVENTION

The inclusion of 2'-O—R substituted nucleosides in ribozymes and antisense oligonucleotides (particularly wherein R is methyl) has been shown to greatly enhance their stability and, hence, their utility. Methods for the synthesis of oligonucleotides containing 2'-O-substituted nucleosides have suffered from the difficulties inherent in the synthesis of individual 2'-O-substituted nucleosides themselves. These difficulties include low yields of the desired product due to non-selective methylation and/or multi-step syntheses, and high costs and/or lengthy synthesis times inherent in prior art methods.

It has been discovered that high yields of 2'-O—R substituted uridine and 2'-O—R substituted cytidine (wherein R is $C_1$–$C_3$ alkyl or allyl) can be produced when unprotected anhydrouridine or anhydrocytidine, respectively, are reacted in the presence of $Mg(OR)_2$ in the corresponding alcohol, ROH. This discovery is unexpected because previous studies suggested that reactions of unprotected anhydrouridine with magnesium methoxide at 100° C. gave no product. (McGee and Zhai, supra).

Thus, in the first aspect, the inventive method comprises the following reaction:

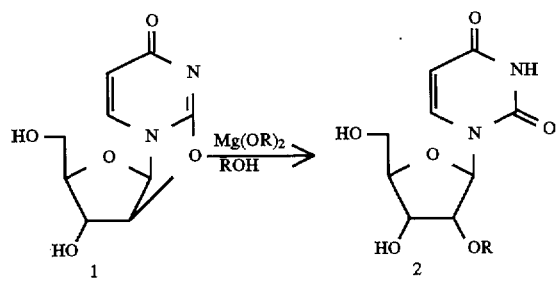

where R is a $C_1$–$C_3$ alkyl or allyl. Preferably R is methyl. The reaction is preferably conducted at about 150° C. Lower temperatures can be used, but the reaction proceeds more slowly. Product has been observed from reaction at 120° C., for example. Higher temperatures can also be employed, but significantly higher temperatures might require larger condensers or cooling equipment.

In a second aspect of the present invention, 2'-O—R substituted cytidine is produced by the same synthetic route:

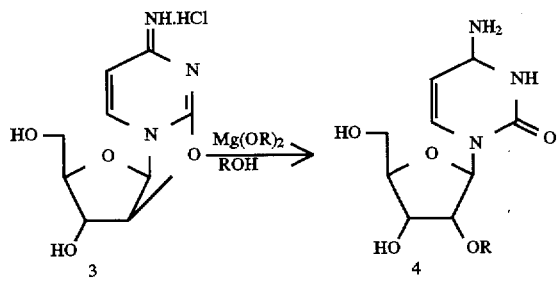

The definition of R and the reaction conditions are the same as for the production of 2'-O—R substituted uridine describe above. In a preferred embodiment, R is methyl.

The synthesis of anhydrouridine (1) from uridine can be conducted according to the method described in Verheyden et al., *J. Org. Chem.* 36:25–254, 1971. Briefly, uridine is reacted with diphenyl carbonate, sodium bicarbonate and DMF at an elevated temperature, preferably 90° C. Uridine (and cytidine) are commercially available from, for example, SIGMA Chemical Co. (St. Louis, Mo.). Diphenyl carbonate, sodium bicarbonate and DMF are all commercially available as well (e.g., ALDRICH, Milwaukee, Wis.).

The synthesis of anhydrocytidine is conducted as described in Kikugawa and Kiyomi, *J. Org. Chem.* 37:284–288, 1972, where cytidine is reacted with a mixture of phosphorous oxychloride and DMF at room temperature.

The utility of 2'-substituted pyrimidine ribonucleosides for incorporation in antisense oligonucleotides and ribozymes to enhance target binding and nuclease resistance is well known to those skilled in the art and has been widely published. See, e.g., Uhlmann and Peymann, *Chem. Rev.* 90: 543, 1990; and *Antisense Research and Applications, supra.* Methods for incorporating 2'-substituted pyrimidine ribonucleosides into oligonucleotides are well known as well. E.g., Sproat and Lamond, supra.

The methods of the present invention are an improvement over prior art methods because they involve fewer steps, higher overall yield, reduced synthesis time, and reduced cost. In particular, the present methods are an improvement over that of McGee and Zhai, supra, because they eliminate the need for ribose protecting groups and utilize the corresponding alcohol as the solvent. As noted previously, McGee and Zhai did not observe any 2'-O-methyluridine product with unprotected anhydrouridine.

Furthermore, synthesis of $Mg(OR)_2$ is conducted in the corresponding alcohol, ROH. Thus, the present methods can be conducted in the same reaction vessel as that in which $Mg(OR)_2$ was synthesized. This simplifies the process. Using the method of McGee and Zhai, it is necessary to isolate $Mg(OR)_2$ from the alcohol-based reaction solution before its addition to the DMF-containing reaction vessel used by McGee and Zhai for alkylation of 5'-protected anhydrouridine.

The improved methods of synthesizing 2'-O-substituted uridine and cytidine ribonucleosides also leads to improved methods of synthesizing oligonucleotides containing them. Thus, in a third aspect, the invention provides an improved method of synthesizing oligonucleotides containing one or more 2'-O-substituted uridine or cytidine residues, the method comprising synthesizing 2'-O-substituted uridine or cytidine according to either of the first two aspects of the invention and then employing the 2'-O-substituted uridine or cytidine so-produced in the synthesis of an oligonucleotide containing one or more of such residues. Oligonucleotide synthesis can be conducted by any suitable means, a number of which are standard and well known to those skilled in the art. E.g., *Methods in Molecular Biology v. 20: Protocols for Oligonucleotides and Analogs* (S. Agrawal, Ed., Humana Press, Totowa, N.J. 1993).

One skilled in the art will recognize that modifications may be made in the present invention without deviating from the spirit or scope of the invention. The invention is illustrated further by the following examples, which are not be construed as limiting the invention or scope of the specific procedures described herein.

EXAMPLES

Example 1

Synthesis of 2'-O-methyl-Uridine 2,2'-anhydro uridine (1, 75 g, 331.56 mmol) was added to the freshly prepared solution of 15% magnesium methoxide (1218.75 ml, 1.66 mol) in methanol. The mixture was refluxed at 150° C. for five hours. The mixture was cooled down to room temperature and then to 5° C. on ice bath. The pH was adjusted to 7 by using glacial acetic acid. The solution was roto-evaporated to a foam. This solid was refluxed with ethyl alcohol (1500 ml) for two hours. The solid was filtered and filtrate was roto-evaporated to a solid mass. The isolated yield of the compound was 78.75 g (92%). The product was >95% pure by HPLC. The yield after quantitation against uridine was 89%. The structure of the compound was confirmed by $^1$H-NMR and elemental analysis. Table 1 shows the PMR results of the compounds.

Example 2

Synthesis of 2'-O-methyl-Cytidine 2,2'-anhydro Cytidine HCl (3, 1 g, 3.82 mmol) was added to the freshly prepared solution of 15% magnesium methoxide (16.25 ml, 22.17 mmol) in methanol. The mixture was refluxed at 150°–160° C. for five hours. The mixture was cooled down to room temperature and then to 5° C. on ice bath. The pH was adjusted to 7 by using glacial acetic acid. The solution was roto-evaporated to a gummy mass. This material was refluxed with ethyl alcohol (25 ml) for two hours. The solid was filtered and filtrate was roto-evaporated to a solid mass. The isolated yield after quantitation against cytidine was 752 mg (76%). The product was >93% pure by HPLC. The structure of the compound was confirmed by $^1$H-NMR and elemental analysis. Table 1 shows the PMR results of the compounds.

TABLE 1

Proton NMR (300 MHz) of 2'-O-methyl nucleosides

| Cmpd | H-1' | H-2' | H-3' | H-4' | H-5'<br>H-5" | H-5 | H-6 | —CH$_3$ |
|---|---|---|---|---|---|---|---|---|
| 2 | 5.90<br>(d, 3.36) | 3.97<br>(m) | 4.27<br>(m) | 4.02<br>(m) | 3.76–3.84<br>(m) | 5.82<br>(d, 7.93) | 7.85<br>(d, 8.09) | 3.45<br>(s) |
| 4 | 5.91<br>(d, 3.33) | 3.95<br>(m) | 4.24<br>(m) | 4.04<br>(m) | 3.76–3.85<br>(m) | 6.01<br>(d, 7.33) | 7.82<br>(d, 7.48) | 3.47<br>(s) |

From the foregoing, it will appreciated that although specific embodiments of the invention have been described herein for purposes of illustration, various modifications may be made without deviating from the spirit or scope of the invention.

What is claimed is:

1. A method of synthesizing 2'-O—R substituted uridine comprising reacting 2,2'-anhydrouridine with Mg(OR)$_2$ in ROH, wherein R is C$_1$–C$_3$ alkyl or allyl.

2. The method according to claim 1, wherein R is methyl.

3. A method of synthesizing 2'-O—R substituted cytidine comprising reacting 2,2'-anhydrocytidine with Mg(OR)$_2$ in ROH, wherein R is C$_1$–C$_3$ alkyl or allyl.

4. The method according to claim 3, wherein R is methyl.

5. A method for synthesizing oligonucleotides containing one or more 2'-O-substituted uridine or cytidine ribonucleotides wherein the improvement is preparing the 2'-O-substituted uridine or cytidine by 1) reacting 2,2'-anhydrouridine or 2,2'-anhydrocytidine with Mg(OR)2 in ROH to produce 2'-O—R substituted uridine or cytidine, respectively, wherein R is C1–C3 alkyl or allyl, 2) isolating the 2'-substituted uridine or cytidine, and 3) using said 2'-O-substituted uridine or 2'-O-substituted cytidine in said synthesis of said oligonucleotides.

6. The method according to claim 5, wherein R is methyl.

* * * * *